(12) United States Patent
Nahm

(10) Patent No.: US 7,888,442 B2
(45) Date of Patent: Feb. 15, 2011

(54) SIZE SELECTIVE CATALYSIS WITH ION EXCHANGE RESINS

(75) Inventor: Steve Nahm, West Milford, NJ (US)

(73) Assignee: Sun Chemical Corporation, Parsippany, NJ (US)

( * ) Notice: Subject to any disclaimer, the term of this patent is extended or adjusted under 35 U.S.C. 154(b) by 475 days.

(21) Appl. No.: 12/113,495

(22) Filed: May 1, 2008

(65) Prior Publication Data

US 2008/0242814 A1    Oct. 2, 2008

Related U.S. Application Data

(62) Division of application No. 11/130,572, filed on May 17, 2005.

(51) Int. Cl.
*C08F 118/02* (2006.01)
*C08F 2/00* (2006.01)

(52) U.S. Cl. .......................... 526/319; 526/89; 526/227

(58) Field of Classification Search .................. 526/89, 526/319, 227

See application file for complete search history.

(56) References Cited

U.S. PATENT DOCUMENTS

| | | | |
|---|---|---|---|
| 5,017,649 A | 5/1991 | Clemens | |
| 5,347,043 A | 9/1994 | Sabahi et al. | |
| 5,350,875 A | 9/1994 | Kumar et al. | |
| 5,496,896 A | 3/1996 | Alfons | |
| 5,536,872 A | 7/1996 | Sabahi et al. | |
| 5,539,017 A | 7/1996 | Rheinberger et al. | |
| 5,945,489 A | 8/1999 | Moy et al. | |
| 6,025,410 A | 2/2000 | Moy et al. | |
| 6,239,321 B1 * | 5/2001 | Mossman et al. | 585/10 |
| 6,657,036 B1 | 12/2003 | Jung et al. | |
| 2004/0072979 A1 | 4/2004 | Sheridan et al. | |

FOREIGN PATENT DOCUMENTS

| | | |
|---|---|---|
| EP | 1431320 | 6/2004 |
| WO | 01/66246 | 9/2001 |
| WO | 2007/000684 | 1/2007 |

OTHER PUBLICATIONS

Choudary, et al. Layered double hydroxide fluoride: a novel solid base catalyst for C-C bond formation, Green Chemistry 3, 257-260, 2001.
Garcia-Serrano, et al. "Catalytic behavior of the microporous hexagonal zincophosphate CZR in base-catalyzed reactions", Studies Surf. Sci. and Catal. 130, 2987-2992, 2000.
Roelofs, et al. "On the structure of activated hydrotalcites as solid base catalysts for liquid-phase aldol condensation", J. Catl. 203, 184-191, 2001.
Bartoli, et al. "Cerium(III) chloride catalyzed michael reaction of 1,3-dicarbonyl compounds and enones in the presence of sodium iodide under solvent-free conditions", Eur. J. Org. Chem., 617-620, 1999.
Kotsuki, et al. "Trifluoromethanesulfonic acid, an unusually powerful catalyst for the michael addition reaction of β-ketoesters under solvent-free conditions", J. Org. Chem. 64, 3770-3773, 1999.
Soriente, et al. "C-C bond formation by catalyzed conjugate addition and alkoxyalkylation of 1,3dicarbonyl compounds", Green Chemistry 1, 157-162, 1999.
Drago and Jurczyk, et al. "Strong solid base reagents and catalysts based on carbonaceous supports", J. Chem. Soc. Perkin Trans. 1, 927-930, 1996.
Li et al. "Use of formic acid in controlling the rate of the michael addition reaction in base catalyzed, thermally cured acetoacetylated acrylic/TMPTA coatings", J. Coat Technol 65, 63-69 1993.
Rector et al. "Applications for acetoacetyl chemistry in thermoset coatings", J. Coat Technol. 61, 31-37, 1989.
International Search Report and Written Opinion of the International Searching Authority issued for related PCT International application No. PCT/US06/19016; Mar. 21, 2008.

* cited by examiner

*Primary Examiner*—Michael M Bernshteyn
(74) *Attorney, Agent, or Firm*—Kramer Levin Naftalis & Frankel LLP

(57) ABSTRACT

A method of preparing oligomeric compounds from polyfunctional reactants in the presence of heterogeneous catalysts that exhibit size selective characteristics, such that further reaction between first generation products or first generation products and reactants is less favored than between the starting reactants is disclosed. Preparation of oligomeric polyacrylate compounds in a liquid solution using these catalysts is also disclosed comprising reacting X—H acidic Michael donor compounds with unsaturated Michael acceptor compounds containing more than one unsaturated group.

16 Claims, 1 Drawing Sheet

SIZE SELECTIVE CATALYSIS WITH ION EXCHANGE RESINS

RELATED APPLICATIONS

This application is a divisional of U.S. application Ser. No. 11/130,572, filed May 17, 2005, now pending, which is hereby incorporated by reference in its entirety.

FIELD OF THE INVENTION

The present invention describes the use of heterogeneous catalysts with size selective characteristics to prepare hyperbranched polyacrylate resins with controlled molecular weight distribution.

BACKGROUND OF THE INVENTION

Polyacrylate functional materials are widely used in coating compositions curable with mechanisms initiated by free radicals (UV/EB, peroxide, etc) or other reactive species, but there are only a limited number of structural variations available as articles of commerce. These materials are currently manufactured primarily by reaction between acrylic acid and polyol or polyepoxy compounds, forming polyacrylic acid esters. While polyol and polyepoxy materials with broad structural variety are generally available articles of commerce, acrylic acid is a corrosive and hazardous material, requiring special handling procedures, rendering this process a specialized conversion. Furthermore, because of the volatility of acrylic acid and its tendency to thermal polymerization, the esterification reaction must be conducted at temperatures below about 125° C., limiting the reaction rate. In some cases, these difficulties may be avoided by transesterification of polyols by acrylic acid esters of the lower alcohols with removal of volatile reaction products to drive the reaction. Although this circumvents the problems associated with handling acrylic acid, it introduces some new ones, which may be more difficult or expensive to overcome. These new problems include handling volatile acrylic monomers, which are both toxic and skin sensitizers, and installation of efficient fractionation equipment to separate the reaction products to be removed, generated during transesterification, from the volatile starting monomers. Also known are methods to make polyacrylate functional compounds from reactions between polyisocyanate containing compounds and hydroxyl containing acrylate esters to make polyurethane polyacrylate materials. However, commodity polyisocyanates are toxic, water sensitive and relatively expensive starting materials with limited structural availability, reducing the appeal of this approach as well.

The Michael addition reaction between low molecular weight C—H acidic donor compounds and electron deficient C═C acceptor compounds is a well-known reaction in the literature of organic chemistry (for example, Choudary, et al., Green Chemistry 3, 257, 2001). A number of catalysts are similarly known to be effective for this reaction (for example, Kotsuki, et al., J. Org. Chem., 64, 3770, 1999 and Bartoli, et al., Eur. J. Org. Chem., 617, 1999, as well as many others), and many have been described (U.S. Pat. No. 5,539,017 and U.S. Pat. No. 5,496,896) as useful in thermal crosslinking of coatings consisting of polyacetoacetate and polyacrylate containing compounds. Ashland, (WO 01/00684 (2001), U.S. Pat. No. 6,025,410 (2000), U.S. Pat. No. 5,945,489 and USP application 20040072979) has recently disclosed using strongly basic soluble catalysts at moderate temperatures to react C—H acidic Michael donor compounds, including beta-dicarbonyl containing resins and nitroaliphatic compounds, with excess low molecular weight polyacrylates to form polyacrylate containing polymers dissolved in polyacrylate diluents in situ for use as ultraviolet light and peroxide curable compositions.

There are, however, drawbacks to these Ashland approaches, in that the materials they describe have only limited storage stability. The unsatisfactory storage stability of the Ashland materials can be attributed to both incomplete reaction between the polyacetoacetates and polyacrylates and to the presence of active catalyst in the final product mixtures.

Furthermore, in order to make liquid compositions suitable for coatings applications in the Ashland patents, a large molar excess of the acrylate C═C groups is generally required, and as the number of acetoacetate or other donor groups on the resin increases, the excess of acrylate C═C acceptor groups must be increased substantially. Additionally, this excess must be significantly larger if the polyacrylate contains more than two C═C groups. Since such large molar acrylate C═C group excesses are required to produce low viscosity liquid compositions, only a minor amount of the acrylated resins formed in situ will be incorporated in the coatings compositions, limiting their contribution to the cured properties obtained. Therefore, most of the properties attained by the final cured coating will be attributed to the cured properties of the polyacrylate acceptors. Because the polyacrylate acceptors contain 2 or more C═C groups per molecule and generally have low equivalent weights per C═C, they tend to give brittle coatings with high shrinkage and poor adhesion when fully cured.

A more recent prior art (European Patent Application 1431320) discloses an improvement over the Ashland art wherein the excess of polyacrylate required to produce a liquid composition is reduced by first reacting the polyacetoacetate resin with a monofunctional Michael acceptor and then reacting the residual acidic C—H sites in the polyacetoacetate with a polyacrylate in the presence of a basic catalyst. As in the Ashland prior art approach, a disadvantage of this approach is the difficulty in controlling the molecular weight of the polyacrylate product resin, producing high viscosity products that still require substantial quantities of diluents to make useful coating compositions.

Also, the Michael reaction between polyacetoacetates and polyacrylates is generally faster than the standard esterification of polyols by acrylic acid, and is very exothermic. As a result, once it has begun, it can be difficult to control the reaction temperature at a commercially useful scale (and in the absence of solvent), potentially leading to the dangerous condition of a runaway reaction.

U.S. Pat. No. 6,657,036 discloses the use of heterogeneous catalysts like ion exchange resins in the preparation of polycondensation resins and polyaddition resins such as polyamides, polyesters, polycarbonates or urea resins. This process describes the polycondensation and polyaddition of low molecular mass compounds permitting the reaction rate to increase without problems using catalysts without thermal damage to the polyaddition resins or polycondensation resins formed. The catalysts employed for this process no longer induce unwanted secondary reactions and are easy to remove after the final step of the reactions. However, this reference does not teach the usefulness of using these catalysts in Michael reactions, nor solely the more than one functional group per molecule of reactants, the absence of monofunctional blocking groups as well as the molar ratios of said reactants in preparing a final product in a liquid medium and with improved properties. Most importantly, this reference does not recognize the unique product distribution obtainable by the practice of the present invention, in particular for molecules with highly branched structures.

Accordingly, there is a need for a class of catalysts for the Michael reaction that do not require either a large excess of polyfunctional Michael acceptors or monofunctional blocking groups to provide useful liquid compositions. It is also important to have a means of controlling product molecular weight separate and distinct from simple statistics through use of a large excess of one of the reactants. In addition, it is desirable not to have active catalyst residues present in the final product which can affect its long term storage stability.

SUMMARY OF THE INVENTION

The present invention provides a method of preparing oligomeric compounds in a liquid solution comprising reacting two or more reactants in the presence of a heterogeneous catalyst that exhibits size exclusion characteristics based on the size of the reactants that interact in its presence such that its catalytic effectiveness decreases as the size of the reactants increases.

The present invention also provides a method of preparing an oligomeric polyacrylate compound in a liquid solution comprising reacting an acidic X—H Michael donor compound containing at least one acidic X—H group with an unsaturated Michael acceptor compound containing one or more carbon to carbon unsaturated groups in the presence of a heterogeneous ion exchange catalyst that contains free basic anions and bound cations, and which exhibits size selective characteristics, wherein X is an atom and the molar ratio of the acceptor groups to the donor groups is less than about 6. It is particularly effective in producing polyacrylate oligomers that are highly branched.

Other objects and advantages of the present invention will become apparent from the following description and appended claims.

DETAILED DESCRIPTION OF THE INVENTION

Figure 1:
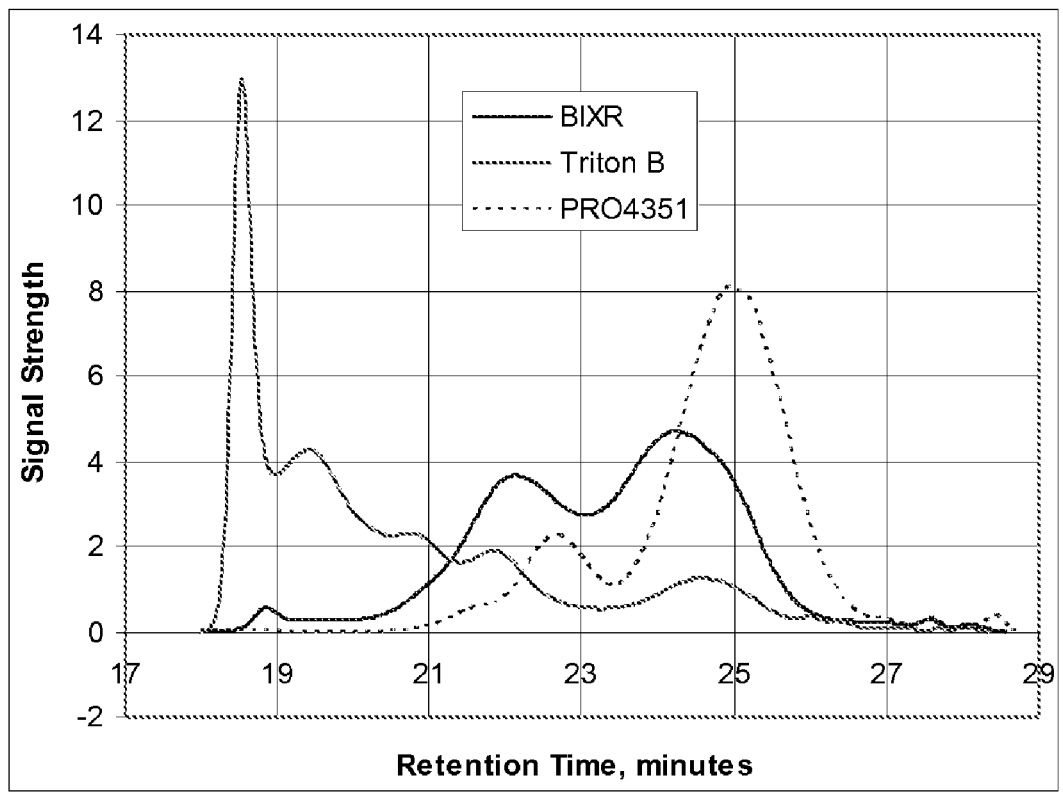
FIG. 1 shows the results of GPC analysis of oligomeric polyacrylate compounds using as catalysts the strongly basic ion exchange resin (BIXR), Sartomer PRO4351 (ethoxylated pentaerythritol triacrylate), or Triton B (benzyl trimethylammonium hydroxide ion exchange resin analogue). The data have been plotted on an equal area basis.

It has been surprisingly found that by replacing the traditional homogeneous catalysts for the Michael reaction with heterogeneous catalysts, a substantial reduction of the excess of C═C acceptor groups is achieved which is required to produce liquid compositions suitable for curable coatings applications. Furthermore, even at these lower molar ratios of acceptor to donor species, products with substantially lower molecular weights are produced.

Preferably, the molar ratio of the acceptor group to the donor group is less than about 6, more preferably less than about 5 and most preferably less than about 4.

Also preferably, the Michael donor compound is selected from the group consisting of X—H acidic compounds where the pKa of the acidic X—H group is less than about 18, preferably less than about 15, and most preferably less than about 12. Such compounds are exemplified by molecules containing structures of the type H—X-$E_1E_2E_3$ where X is carbon and E can be independently selected from hydrogen or electron withdrawing groups such as carbonyl, nitrile, sulfonyl, or nitro, and where no more than 2 of the substituents E on the acidic carbon are hydrogen. For $E_1$=H, $E_2$ and $E_3$ can be connected in a ring structure, and in this case, the ring can also be cyclopentadiene or a ring substituted derivative of cyclopentadiene. Additionally, such compounds are exemplified by molecules containing structures of the type H—X-$E_1E_2$ where X is nitrogen and E can be independently selected from hydrogen or electron withdrawing groups such as carbonyl, sulfonyl, nitrile, or nitro, and where no more than 1 of the substituents E on the acidic nitrogen are hydrogen. When neither $E_1$ nor $E_2$ are H, they can be connected in a ring structure. X can also be other acidic atoms such as O, S, or P.

Again preferably, the Michael acceptor compound contains carbon to carbon double or triple bonds attached directly to one or more electron withdrawing groups such as carbonyl, sulfonyl, nitrile, or nitro, exemplified by vinyl ketones, acrylate esters, maleate and fumarate esters, acetylene dicarboxylate esters, acrylonitrile derivatives, vinyl sulfones or sulfonates, nitro olefins, or the like. Most preferably, the Michael acceptor compound is a polyacrylate compound.

It has also been unexpectedly found that the need for monofunctional blocking acceptors that limit the molecular weight of products made with homogeneous catalysts can be eliminated altogether, and still be able to obtain liquid compositions, without requiring large excesses of multifunctional Michael acceptors, by employing size selective heterogeneous catalysts based on ion exchange resins.

As indicated previously, Michael donors and acceptors are known to react together under catalysis of strong bases. It is also known to use similar soluble strong base catalysts to cure coating compositions that contain both Michael donor and acceptor components (U.S. Pat. No. 5,017,649 and, Rector, et al., J. Coat Technol., 61, 31, 1989). It has also been recognized that such coatings compositions which contain basic catalysts are not storage stable, and therefore the catalyst must be added shortly before application to the substrate to accommodate the short pot life of the catalyzed compositions (Li and Graham, J. Coat Technol, 65, 63, 1993). Incorporation of a volatile strong acid can overcome the storage stability problems in precatalyzed coatings compositions. Such a fugitive acid effectively blocks the catalyst activity during storage, but when heated, it readily evaporates from the coated surface, allowing the unblocked catalyst to function, providing coatings without loss of cured properties. However, such volatile acids are corrosive towards coating equipment, harmful to the environment, and hazardous to workers.

The curable liquid compositions of the present invention can be prepared substantially free from any Michael reaction catalyst residues by employing catalysts that are insoluble in the reaction mixture. The use of solid insoluble catalysts for the Michael reaction between C—H acidic donor compounds and electron deficient C═C acceptor compounds is well known (WO 01/066246). However, most applications described are limited to small molecule ("fine") chemistry and stress enhanced product selectivity, in particular, towards mono C-alkylation of the Michael donor. One group of patents (U.S. Pat. No. 5,536,872, U.S. Pat. No. 5,350,875, and U.S. Pat. No. 5,347,043) teaches formation of mixtures of materials which may not be considered "fine chemicals", but which nevertheless are of low molecular weight, and which do not contain any residual unsaturation in the final products, in contrast to the products made by the preferred catalysts and processes of this invention.

There are a variety of advantages to the use of an insoluble catalyst in any process where isolation of the end product is desired. These advantages include the ability to easily remove the catalyst from the product without expensive and time consuming wet chemical "work up" procedures, by simple filtration or by employing the catalyst, for example, in a fixed bed. The product can then be obtained substantially free from catalyst residues, which residues may have an impact on further desirable or undesirable transformations of the product, such as its further reactions to the ultimate desired product, or its storage stability. Reaction exotherms can be controlled by the use of simple engineering controls such as the amount of catalyst and length contact time, and a fixed bed can be designed with external heat management capability, including both heating and cooling capacity. By using a fixed bed, the process stream can be repeatedly cycled through the bed under conditions that produce only fractional conversion per cycle, until the desired product composition is obtained. This approach further controls the rate of heat generated by the reaction, improving process control. Oftentimes, the catalyst can be reused directly, or after simple regeneration procedures, avoiding formation of potentially hazardous water streams for disposal, which contribute to the cost of the product, and may pollute the environment.

While these advantages have been previously recognized (U.S. Pat. No. 5,536,872, U.S. Pat. No. 5,350,875), the products made were not the higher molecular weight, highly branched resins of this invention. In particular, the preferred products were made from the reaction between monofunctional Michael donors and acceptors, such that there were no pendant acceptor groups present on the final products. Furthermore, the preferred products were made in such a way as to consume all of the Michael acceptor components, so that no residual unreacted acceptor species remained in the reaction mixture.

Simple inorganic bases, for example, sodium, potassium, calcium and barium hydroxide, and potassium carbonate, can function as effective catalysts for Michael reaction between polyacetoacetates and polyacrylates. However, they eventually dissolve in the reaction medium, and gel permeation chromatography (GPC) has demonstrated that they provide product distributions very similar to those provided by the traditional soluble catalysts (strong tertiary amine bases). As shown below, the preparation of highly branched oligomeric polyacrylate compounds in a liquid solution cannot be practiced using these catalysts since their use results in gelled reaction mixtures, presumably due to formation of the soluble intermediate enolate anion, which functions as a homogeneous basic catalyst.

It has been recognized that topographical characteristics of insoluble solid catalysts can play an important role in the rate and course of the Michael reaction (WO #0166246). A better known example of topographical effects on reactivity from the organic chemical literature is the increasing difficulty during hydrogenation of simple carbon to carbon multiple bonds as the steric environment around the target site becomes more congested. This is attributed to the reduced ability of the target carbon to carbon multiple bonds to both approach closely enough and properly orient with regard to the catalytically active surface. If the target site cannot "sit down" on the catalytically active surface, reaction will not take place. In other cases, there has been no recognition of this feature (U.S. Pat. No. 5,536,872 and U.S. Pat. No. 5,350,875). For example, there is a critical relationship between the size of the molecules reacting and their access to the catalytically active site on or in a solid catalyst (Garcia-Serrano, et al., Studies Surf. Sci. and Catal., 130, 2987, 2000; and Soriente, et al., Green Chemistry, 1, 157 (1999), Drago and Jurczyk, et al., J. Chem. Soc. Perkin Trans. 1, 927, 1996). In one recent example of Michael reactions from "fine" chemistry, the claimed advantages of the heterogeneous catalyst were based on the larger pore size within its structure, allowing reactants better access to the active centers (WO 01/66246). Various catalyst activation treatments have been recognized as creating improved access to edge and corner sites (Roelofs, et al., J. Catl. 203, 184, 2001).

By using catalysts insoluble in the reaction medium, and in particular, catalysts where the active sites are not readily accessible to larger molecules, the resultant product distribution will be skewed towards products derived from reactions between smaller molecules. This product distribution is a direct consequence of the steric constraints imposed by heterogeneous catalysts, particularly where the catalytic sites are shielded from the bulk reaction medium. In these cases, they rely on the diffusion of reactants into the active centers (turbulence and bulk mixing are not adequate to drive contact between catalyst site and the reactants) and reactions between larger molecules are much less favorable than between small molecules. In particular, active centers that combine specific chemical interactions with size exclusion will further preferentially select between potential reactants. For example, a catalytically active site that is also ionic will select for the more polar reactants in a mixed feed due to the improved ability of the more polar reactants to "solvate" the charge at the catalytically active center. Homogeneous catalysts do not promote a product distribution favoring products from small molecule reactions because any spatial constraints imposed on the reactants are less effective than by a catalyst surface.

When these principles are applied to the Michael reaction between multifunctional donor and acceptor molecules, further reactions between the initial (first generation) products, including gelation, will be prevented, even at reactant ratios without the large molar excesses of acceptor species taught by Ashland (WO 01/00684 (2001), U.S. Pat. No. 6,025,410 and U.S. Pat. No. 5,945,489). These large molar ratios are required by the prior art, which relies on statistics alone to produce liquid products under homogeneous catalysis, based on their tendency towards further reaction through the pendant acceptor groups to form second and higher generation products as the average pendant reactive functionality per molecule increases.

Consequently, manufacture of highly branched molecules from multifunctional starting materials using catalysts of the type disclosed in this invention provides an advantage over prior art in that useful liquid compositions can be prepared without requiring a large excesses of one reagent or the other, or even chain terminators (monofunctional blocking groups). Furthermore, product compositions produced by size selective catalysts, result in liquid resinous products of particularly low viscosity compared to prior art, which require less additional reactive diluent to formulate into coatings with useful viscosities, and can thus contribute an even larger proportion of the final cured coatings properties.

Catalysts which are most preferred by this invention are insoluble in the reaction medium, and in particular, have their active sites substantially contained within a microporous structure, or are otherwise subject to effects of steric hindrances. In particular, ion exchange resins are effective catalysts for this reaction and provide such size selective catalytic properties. Examples of catalytically active solids with these structural constraints are commercially available under the Amerlyst or Dowex trade names. Catalysts effective for the Michael reaction are characterized as containing strongly basic anions such as hydroxide or halogen anions, fluoride in particular, present as exchangeable counter ion to a bound cationic site, such as quaternary nitrogen or phosphorus. These catalytic centers may be advantageously employed in the practice of this invention whether incorporated within synthetic polymeric supports or within modified mineral supports such as zeolites.

These principles have been illustrated using strongly basic ion exchange resins to make products by the Michael reaction, but can be applied to other reaction types as well, by using ion exchange resins with other bound and exchangeable ionic parts.

Example 1

Catalyst Screening Evaluations to Make Linear Oligomers with Reactive End Groups In the absence of solvent, half a mole each of the difunctional acidic C—H donor ethyl acetoacetate, (EtOAcAc; D, Aldrich) and the difunctional C=C acceptor tripropyleneglycol diacrylate (TPGDA; A, Cognis) in a 1:1 equivalent ratio of donor sites (C—H) to acceptor sites (C=C), were combined in a 500 ml round bottomed flask fitted with a mechanical stirrer, temperature probe and condenser, and heated by an electrical heating mantle. After an amount of catalyst was added and the mixture heated to the 50° C. set point, samples were periodically withdrawn to measure product viscosity development after reaction exotherm. The reaction mixtures were then maintained at 60° C. for several hours. The samples were analyzed by GPC to determine oligomer distribution changes during the course of the reaction. Table 1 compares weight percent oligomer distribution obtained for several catalysts at approximately equal product viscosity.

This example clearly shows the preference of the size selective catalyst (BIXR) to consume the smaller reactants, especially A and AD, and selectively form the group of oligomers DADAD, ADADA, and ADADAD without formation of substantial amounts of higher oligomers.

Example 2

Preparation of a Polyfunctional Acidic C—H Donor

Into a 2,0000 ml flask, fitted with a mechanical stirrer, distillation column and head, nitrogen inlet tube and temperature probe, was charged powdered sorbitol (564.73 g, Aldrich) and tert-butyl acetoacetate (1226.0 g, Eastman Chemical Co.). The mixture was heated to 105° C. with slow stirring until all the sorbitol had melted and then stirring was increased with heating to 135° C., where the pot temperature was maintained until over 90% of theoretical tert-butanol was collected. The pot temperature was then raised to 165° C. over an hour and distillation continued until all the expected tert-butanol was collected. The mixture was cooled, and the apparatus reconfigured for vacuum stripping whereupon residual volatiles were removed at a pot temperature of 120° C. The product was a heavy syrup of low color. The average degree of acetoacetate substitution was 2.50.

Example 3

Catalyst Comparison to Make Highly Branched Oligomers with Pendant Reactive Groups The polyfunctional acidic C—H donor compound from Example 2 (sorbitol-(OAcAc)$_{2.5}$, D) and a trifunctional C=C acceptor (trimethylolpropane triacrylate TMPTA, Cognis, A) in a 1:1 equivalent ratio of C—H:C=C were dissolved in reagent grade denatured ethanol solvent and reacted in the presence of a basic catalyst as detailed below in Table 2. The mixture catalyzed by $K_2CO_3$ gelled within 1 hour, while the mixture catalyzed by the strongly basic ion exchange resin (BIXR) remained liquid for 24 hours in spite of the fact that nearly all of the TMPTA was consumed during this time. Table 3 below also compares the acceptor/donor functionality and equivalent ratios as well as the status of the final reaction product of a Michael addition reaction using the previously described Ashland procedure versus the procedure of the present invention.

TABLE 1

| Oligomer Type, wt % | Catalyst[1], wt % | | | | | | | |
|---|---|---|---|---|---|---|---|---|
| | TOP 0.35 | DBU 0.47 | Ba(OH)$_2$ 0.50 | Ba(OH)$_2$ 0.63 | $K_2CO_3$ 0.46 | $Na_3PO_4$ 0.46 | KF 5.10 | BIXR 5.10 |
| A | 12 | 14 | 9 | 7 | 9 | 9 | 9 | 4 |
| AD | 21 | 19 | 31 | 27 | 25 | 28 | 26 | 8 |
| DAD ADA DADA | 11 | 9 | 22 | 20 | 19 | 21 | 19 | 14 |
| DADAD ADADA ADADAD | 31 | 32 | 28 | 31 | 30 | 30 | 31 | 40 |
| Higher | 24 | 26 | 9 | 13 | 15 | 12 | 14 | 15 |
| Viscosity cps @25° C. | 106 | 119 | 115 | 155 | 155 | 152 | 164 | 111 |

[1]TOP = tri(n-octyl)phosphine (Aldrich); DBU = 1,8-diazabicyclo[5.4.0]undec-7-ene (Aldrich); BIXR = water-wet Amberlyst A26 OH basic ion exchange resin (Rohm and Haas)

TABLE 2

| Catalyst | g Catalyst | g Sorbitol-(OAcAC)$_{2.5}$ | g TMPTA | C—H:C═C ratio | g Ethanol |
|---|---|---|---|---|---|
| K$_2$CO$_3$ | 0.90 | 38.93 | 49.56 | 0.997 | 145.0 |
| BIXR | 3.20 | 38.91 | 49.30 | 1.000 | 90.0 |

TABLE 3

Information from Table 3 of Ashland Patents 5,945,489 and 6,025,410

| Michael Addition Reaction | | Function-ality Ratio | Equiv-alent Ratio | Wt % Donor | Reaction Product |
|---|---|---|---|---|---|
| Acceptor | Donor | | | | |
| TMPTA | Neopentyl glycol diacetoacetate | 3:4 3:4 | 6.2:1 2.9:1 | 10 15 | sol gel |
| TMPTA | Glycerine triacetoacetate | 3:6 3:6 | 7.2:1 5.2:1 | 7.5 10 | sol gel |
| Experimental (present invention) | | | | | |
| TMPTA | Sorbitol(OAcAc)$_{2.5}$ | 3.5 | 1.0:1 | 44 | sol |

Example 4

Use of BIXR to Make Highly Branched Oligomers with Pendant Reactive Groups

Into a 500 ml flask fitted with a mechanical stirrer, a reflux condenser, an air inlet tube and temperature probe was charged ethyl acetoacetate (Aldrich, 26.03 g), Sartomer PRO4351 (ethoxylated pentaerythritol triacrylate, 107.10 g), water-wet Amberlyst A260H (Rohm and Haas, strongly basic quaternary ammonium hydroxide ion exchange resin, 20.0 g, equivalent to 7.90 g on a dry basis), a free radical polymerization inhibitor (Eastman, p-methoxyhydroquinone, MEHQ, 0.045 g), and denatured ethanol (130 g). The mixture had a nominal C—H to C═C ratio of 1.00:1.65. The contents of the flask were heated at 60° C. under gentle stirring until GPC analysis showed all the starting materials had been consumed. The mixture was filtered to remove the catalyst and stripped at reduced pressure on a rotary evaporator to remove the ethanol solvent. The product was low in viscosity and of light color.

Comparative Example

Use of Soluble BIXR Active Site Analogue to make Highly Branched Oligomers with Pendant Reactive Groups Into a 250 ml flask fitted with a mechanical stirrer, air inlet tube and temperature probe was charged ethyl acetoacetate (Aldrich, 26.06 g), Sartomer PRO4351 (ethoxylated pentaerythritol triacrylate, 155.58 g), Triton B (Aldrich, benzyl trimethylammonium hydroxide as a 40% solution in methanol, a strongly basic quaternary ammonium hydroxide ion exchange resin analogue, 0.92 g), and a free radical polymerization inhibitor (Eastman, p-methoxyhydroquinone, MEHQ, 0.050 g). The mixture had a nominal C—H to C═C ratio of 1.00 to 2.25. The contents of the flask were mixed without heating whereupon an exothermic reaction ensued. After 3 hours, the viscous mixture was quenched with 2.5 g of a 1.0N solution of HCl. The product was high in viscosity and of light color.

The results of GPC analysis of these experiments are shown in FIG. 1, where the data have been plotted on an equal area basis. Low molecular weight materials are retained for longer times on the column, and appear towards the right on the graph. Higher molecular weight materials are less well retained by the column and appear towards the left. The excluded volume of this column set (100A, 50A, 50A, 50A) occurs at times earlier than about 19 minutes, where molecules larger than the pore sizes of the column packing elute. FIG. 1 clearly shows the unique product distribution available by the practice of this invention relative to homogeneous catalysis.

The invention has been described in terms of preferred embodiments thereof, but is more broadly applicable as will be understood by those skilled in the art. The scope of the invention is only limited by the following claims.

What is claimed is:

1. A method of preparing an oligomeric polyacrylate compound in a liquid solution comprising reacting an acidic X—H Michael donor compound containing at least one acidic X—H group with an unsaturated Michael acceptor compound containing one or more carbon to carbon unsaturated groups in the presence of a heterogeneous ion exchange catalyst that contains free basic anions and bound cations, and which exhibits size selective characteristics, wherein X is an atom independently selected from the group consisting of C, N, O, S and P, and the molar ratio of the acceptor groups to the donor groups is less than about 6, wherein said acidic X—H Michael donor compound has an acidic X—H group with a pKa of less than about 18.

2. The method of claim 1, wherein the molar ratio of the acceptor groups to the donor groups is less than about 5.

3. The method of claim 1, wherein the molar ratio of the acceptor groups to the donor groups is less than about 4.

4. The method of claim 1, wherein said Michael donor compound contain a structure of the type H—X-E1E2E3, wherein X is carbon and E1E2E3 are substituents on the carbon atom and are independently selected from the group consisting of hydrogen, and an electron withdrawing group independently selected from the group consisting of carbonyl, sulfonyl, nitrile and nitro, wherein no more than 2 of the substituents E on the carbon atom are hydrogen.

5. The method of claim 4, wherein E1 is a hydrogen and E2 and E3 are connected in a ring structure.

6. The method of claim 5, wherein said ring is a cyclopentadiene or a ring substituted derivative of cyclopentadiene.

7. The method of claim 1, wherein said Michael donor compound contain a structure of the type H—X-E1E2 wherein X is nitrogen and E1E2 are substituents on the nitrogen atom and are independently selected from the group consisting of hydrogen and an electron withdrawing group independently selected from the group consisting of carbonyl, sulfonyl, nitrile and nitro, wherein no more than 1 of the substituents E on the nitrogen atom is hydrogen.

8. The method of claim 7, wherein neither E1 nor E2 are H, and E1 nor E2 are connected in a ring structure.

9. The method of claim 1, where X is carbon and said Michael donor compound is a 1,3-dicarbonyl compound.

10. The method of claim 1, wherein X is nitrogen and said Michael donor compound contains the partial structure H(E)N—((C=O)—Y) where E is a hydrogen or another atom and Y is selected from the group consisting of carbon, nitrogen and oxygen atom, and wherein E and Y are connected through a ring formed by 1 or more intervening, connected atoms.

11. The method of claim 1, wherein said Michael acceptor compound contains carbon to carbon multiple bonds attached directly to one or more electron withdrawing groups.

12. The method of claim 1, wherein said Michael acceptor compound is a polyacrylate compound.

13. The method of claim 1, wherein said Michael acceptor compound is selected from the group consisting of vinyl ketones, maleate esters, fumarate esters, acetylene dicarboxylate esters, acrylonitrile derivatives, vinyl sulfones, vinyl sulfonates and nitro olefins.

14. The method of claim 1, wherein said reaction is carried out in the absence of monofunctional carbon to carbon unsaturated Michael acceptor compounds as blocking groups.

15. The method of claim 1, wherein the oligomeric polyacrylate compound does not contain catalyst residues.

16. An oligomeric polyacrylate compound prepared by the method of claim 1.

* * * * *